United States Patent [19]
Dolle et al.

[11] Patent Number: 5,834,514
[45] Date of Patent: Nov. 10, 1998

[54] HALOMETHYL AMIDES AS IL-1β PROTEASE INHIBITORS

[75] Inventors: Roland E. Dolle, King of Prussia; James M. Rinker, Reading, both of Pa.

[73] Assignee: Vertex Pharmaceuticals, Incorporated, Cambridge, Mass.

[21] Appl. No.: 748,117

[22] Filed: Nov. 12, 1996

Related U.S. Application Data

[63] Continuation of Ser. No. 453,122, May 30, 1995, abandoned.

[51] Int. Cl.⁶ .................................................. A61K 31/16
[52] U.S. Cl. ....................... 514/629; 514/521; 514/628; 514/630; 514/523; 514/524; 514/885; 514/886; 514/921
[58] Field of Search .................................. 514/628, 629, 514/630, 521, 523, 524, 885, 886, 921; 564/209, 210, 211, 212; 558/404

[56] References Cited

FOREIGN PATENT DOCUMENTS 1806291  10/1968  Germany.

*Primary Examiner*—Shailendra Kumar
*Attorney, Agent, or Firm*—Fish & Neave; James F. Haley, Jr., Esq.; Lisa A. Dixon

[57] ABSTRACT

Disclosed are compounds, compositions and methods for inhibiting interleukin-1β protease activity, the compounds having the formula A described herein.

12 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO (iv) ANTI-SENSE: NO (ix) FEATURE:
    (A) NAME/KEY: Modified-site
    (B) LOCATION: 1
    (D) OTHER INFORMATION: /product="OTHER"
        / note= "alanine is derivatized with TRITC - tetra-methylrhodamine isothiocyanate"

(ix) FEATURE:
    (A) NAME/KEY: Modified-site
    (B) LOCATION: 10
    (D) OTHER INFORMATION: /product="OTHER"
        / note= "serine carboxylic acid is derivatized as an amide"

(xi) SEQUENCE DESCRIPTION: SEQ ID NO:1:

Ala  Tyr  Val  His  Asp  Ala  Pro  Val  Arg  Ser
1                  5                        10

HALOMETHYL AMIDES AS IL-1β PROTEASE INHIBITORS

This application is a continuation of application Ser. No. 08/453,122 filed on May 30, 1995, abandoned.

BACKGROUND OF THE INVENTION

1. Field of the Invention

This invention relates to a series of novel non-peptides which exhibit selective in vitro and in vivo inhibition of interleukin-1β converting enzyme, to compositions containing the novel non-peptides and to methods for therapeutic utility. More particularly, the interleukin 1β converting enzyme inhibitors described in this invention comprise novel α-halomethyl amides and α-halomethyl sulfonamides which possess particular utility in the treatment of inflammatory and immune-based diseases of lung, central nervous system, and connective tissues.

Reported Developments

Interleukin-1β (IL-1β) protease (also known as interleukin-1β converting enzyme or ICE) is the enzyme responsible for processing of the biologically inactive 31 kD precursor IL-1β to the biologically active 17 kD form (Kostura, M. J.; Tocci, M. J.; Limjuco, G.; Chin, J.; Cameron, P.; Hillman, A. G.; Chartrain, N. A.; Schmidt, J. A., *Proc. Nat. Acad. Sci.*, (1989), 86, 5227–5231 and Black, R. A.; Kronheim, S. R.; Sleath, P. R., *FEBS Let.*, (1989), 247, 386–391). In addition to acting as one of the body's early responses to injury and infection, IL-1β has also been proposed to act as a mediator of a wide variety of diseases, including rheumatoid arthritis, osteoarthritis, inflammatory bowel disease, sepsis, acute and chronic myelogenous leukemia and osteoporosis (Dinarello, C. A.; Wolff, S. M., *New Engl. J. Med.*, (1993), 328, 106). A naturally occurring IL-1β receptor antagonist has been used to demonstrate the intermediacy of IL-1β in a number of human diseases and animal models (Hannum, C. H.; Wilcox, C. J.; Arend, W. P.; Joslin, G. G.; Dripps, D. J.; Heimdal, P. L.; Armes, L. G.; Sommer, A.; Eisenberg, S. P.; Thompson, R. C., *Nature*, (1990), 343, 336–340; Eisenberg, S. P.; Evans, R. J.; Arend, W. P.; Verderber, E.; Brewer, M. T.; Hannum, C. H.; Thompson, R. C., *Nature* (1990), 343, 341–346; Ohlsson, K.; Bjork, P.; Bergenfeldt, M.; Hageman, R.; Thompson, R. C., *Nature*, (1990), 348, 550–552; Wakabayashi, G., *FASEB*, (1991), 338–343; Pacifici, R.; et al. *Proc. Natl. Acad. Sci.* (1989), 86, 2398–2402 and Yamamoto, I.; et al. *Cancer Rsh* (1989), 49, 4242–4246). The specific role of IL-1β in inflammation and immunomodulation is supported by the recent observation that the cowpox virus employs an inhibitor of ICE to suppress the inflammatory response of its host (Ray, C. A. et al, *Cell*, (1992), 69, 597–604).

In summary, the utility of ICE inhibitors in modifying certain IL-1 mediated disease states has been suggested and demonstrated in vivo by several workers in the field. The following review of the current state of the art in ICE research further supports such utility of ICE inhibitors:

1) WO 9309135, published 11 May 1993, teaches that peptide-based aspartic acid arylacyloxy-and aryoxymethyl ketones are potent inhibitors of ICE in vitro. These compounds also specifically inhibited ICE in the whole cell (in vivo) by their ability to inhibit the formation of mature IL-1β in whole cells. These ICE inhibitors also demonstrated utility in reducing fever and inflammation/swelling in rats.

2) Patients with Lyme disease sometimes develop Lyme arthritis. *B. burgdorferi*, the causative agent of Lyme disease, is a potent inducer of IL-1 synthesis by mononuclear cells. Miller et al. (Miller, L.C.; Lynch, E. A. Isa, S.; Logan, J. W.; Dinarello, C. A.; and Steere, A. C., "Balance of synovial fluid IL-1β and IL-1 Receptor Antagonist and Recovery from Lyme arthritis", *Lancet* (1993) 341; 146–148) showed that in patients who recovered quickly from Lyme Arthritis, the balance in synovial fluid of IL-1-beta and IL-1 ra was in favor of IL-ra. When the balance was shifted in favor of IL-1β, it took significantly longer for the disease to resolve. The conclusion was that the excess IL-1 ra blocked the effects of the IL-1β in the patients studied.

3) IL-1 is present in affected tissues in ulcerative colitis in humans. In animal models of the disease, IL-1β levels correlate with disease severity. In the model, administration of 1 L-1 ra reduced tissue necrosis and the number of inflammatory cells in the colon.

See, Cominelli, F.; Nast, C. C.; Clark, B. D.; Schindler, R., Llerena, R.; Eysselein, V. E.; Thompson, R. C.; and Dinarello, C. A.; "Interleukin-1 Gene Expression, Synthesis, and Effect of Specific IL-1 Receptor Blockade in Rabbit Immune Complex Colitis" *J. Clin. Investigations* (1990) Vol. 86, pp, 972–980.

4) IL-1 ra supresses joint swelling in the PG-APS model of arthritis in rats. See Schwab, J. H.; Anderle, S. K.; Brown, R. R.; Dalidorf, F. G. and Thompson, R. C., "Pro- and Anti-inflammatory Roles of Interelukin-i in Recurrence of Bacterial Cell Wall-induced Arthritis in Rats". *Infect Immun.* (1991) 59; 4436–4442.

5) IL-1 ra shows efficacy in an small open-label human Rheumatoid Arthritis trial. See, Lebsack, M. E.; Paul, C. C.; Bloedow, C. C.; Burch, F. X.; Sack, M. A.; Chase, W., and Catalano, M. A. "Subcutaneous IL-1 Receptor Antagonist in Patients with Rheumatoid Arthritis", *Arth. Rheum.* (1991) 34; 545.

6) IL-1 appears to be an autocrine growth factor for the proliferation of chronic myelogenous leukemia cells. Both IL-1 ra and sIL-1 R inhibit colony growth in cells removed from leukemia patients.

See, Estrov, Z.; Kurzrock, R.; Wetzler, M.; Kantarjian, H.; Blake, M.; Harris, D.; Gutterman, J. U.; and Talpaz, M., "Supression of Chronic Myelogenous Leukemia Colony Growth by Interleukin-1 (IL-1) Receptor Antagonist and Soluble IL-1 Receptors: a Novel Application for Inhibitors of IL-1 Activity". *Blood* (1991) 78; 1476–1484.

7) As in 6) above, but for acute myelogenous leukemia rather than chronic myelogenous leukemia.

See, Estrov, Z.; Kurzrock, R.; Estey, E.; Wetzler, M.; Ferrajoli, A.; Harris, D.; Blake, M.; Guttermann, J. U.; and Talpaz, M. "Inhibition of Acute Myelogenous Leukemia Blast Proliferation by Interleukin-1 (IL-1) Receptor Antagonist and Soluble IL-1 Receptors". (1992) *Blood*79; 1938–1945.

An effective therapy has yet to be fully developed commercially for the treatment of IL-1β mediated inflammatory diseases. Consequently, there is a need for therapeutic agents effective in the treatment and prevention of these diseases.

SUMMARY OF THE INVENTION

According to the present invention, there is provided a compound of the formula (A) or a pharmaceutically acceptable salt thereof:

wherein:
Y=CO or SO$_2$;
R$_1$=independently selected from alkyl, haloalkyl and alkoxyalkyl;

$R_2$=H, alkyl, (CH$_2$)-alkenyl, aralkyl, heteroaralkyl, carboxyalkyl, cyanoalkyl, aryl, heteroaryl; and
$R_3$=H, alkyl, (CH$_2$)-alkenyl, aralkyl, heteroaralkyl, aryl, heteraryl;

"Alkyl" is defined as a saturated aliphatic hydrocarbon which may be either straight- or branched chain. Preferred groups have no more than 12 carbon atoms and may be methyl, ethyl, and structural isomers of propyl, butyl, up to dodecyl.

"Haloalkyl" is defined as an alkyl radical substituted by one or more halogen (F, Cl, Br, I). For example chloromethyl, dichloromethyl, fluoromethyl, difluoromethyl, fluorochloromethyl.

"Alkoxyalkyl" is defined as an alkyl radical substituted by an alkoxy group. For example methoxymethyl.

"Aryl" is defined as a phenyl or naphthyl ring which may be unsubstituted or substituted wherein one or more of the hydrogen atoms has been replaced by the same or different substituents including halo, alkyl, aryl, nitro, cyano, amino, alkylacylamino, hydroxyl, alkoxy, haloalkyl.

"Halo" means iodo, bromo, chloro, fluoro.

"Carboxyalkyl" means an alkyl radical substituted by a carboxyl group. For example, carboxymethyl.

"Aralkyl" means an alkyl radical substituted with an aryl ring. For example benzyl, 4-chlorobenzyl.

"Heteroaryl" means pyridyl, thienyl or furanyl and structural isomers thereof.

"Heteroaralkyl" means an alkyl radical substituted by an heteroaryl ring. For example 2-thienyl ethyl.

"Alkenyl" is defined as an alkyl group containing one or more sites of unsaturation. For example, ethenyl, ethynl, 1-butenyl, 2-butynyl, 1,3-hexadienyl.

"Cyanoalkyl" means an alkyl radical substituted by a cyano group. For example, cyano ethyl.

The present invention also concerns the pharmaceutical composition and method of treatment of IL-1β protease mediated disease states or disorders in a mammal in need of such treatment comprising the administration of IL-1β protease inhibitors of formula (A) as the active agent. These disease states and disorders include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, immune-based diseases, such as hypersensitivity; auto-immune diseases, such as multiple sclerosis; bone diseases; and certain tumors and leukemias.

The present invention has particular utility in the modulation of processing of IL-1β for the treatment of rheumatoid arthritis. Levels of IL-1β are known to be elevated in the synovial fluid of patients with the disease. Additionally, IL-1β stimulates the synthesis of enzymes believed to be involved in inflammation, such as collagenase and PLA2, and produces joint destruction which is very similar to rheumatoid arthritis following intra-articular injection in animals.

In the practice of this invention an effective amount of a compound of the invention or a pharmaceutical composition thereof is administered to the subject in need of, or desiring, such treatment. These compounds or compositions may be administered by any of a variety of routes depending upon the specific end use, including orally, parenterally (including subcutaneous, intraarticular, intramuscular and intravenous administration), rectally, buccally (including sublingually), transdermally or intranasally. The most suitable route in any given case will depend upon the use, the particular active ingredient, and the subject involved. The compound or composition may also be administered by means of controlled-release, depot implant or injectable formulations as described more fully herein.

In general, for the uses as described in the instant invention, it is expedient to administer the active ingredient in amounts between about 0.1 and 100 mg/kg body weight, most preferably from about 0.1 to 30 mg/kg body weight for human therapy, the active ingredient will be administered preferably in the range of from about 0.1 to about 20–50 mg/kg/day. This administration may be accomplished by a single administration, by distribution over several applications or by slow release in order to achieve the most effective results. When administered as a single dose, administration will most preferably be in the range of from about 0.1 to mg/kg to about 10 mg/kg.

The exact dose and regimen for administration of these compounds and compositions will necessarily be dependent upon the needs of the individual subject being treated, the type of treatment, and the degree of affliction or need. In general, parenteral administration requires lower dosage than other methods of administration which are more dependent upon absorption.

A further aspect of the present invention relates to pharmaceutical compositions comprising as an active ingredient a compound of the present invention in admixture with a pharmaceutically acceptable, non-toxic carrier. As mentioned above, such compositions may be prepared for use for parenteral (subcutaneous, intraarticular, intramuscular or intravenous) administration, particularly in the form of liquid solutions or suspensions; for oral or buccal administration, particularly in the form of tablets or capsules; or intranasally, particularly in the form of powders, nasal drops or aerosols.

When administered orally (or rectally) the compounds will usually be formulated into a unit dosage form such as a tablet, capsule, suppository or cachet. Such formulations typically include a solid, semi-solid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, aginates, tragacanth, gelatin, syrup, methylcellulose, polyoxyethylene sorbitar monolaurate, methyl hydroxybenzoate, propyl hydroxybenzoate, talc, and magnesium stearate.

The compositions may be prepared by any of the methods well-known in the pharmaceutical art, for example as described in *Remington's Pharmaceutical Sciences,* 17th edition, Mack Publishing Company, Easton, Pa., 1985. Formulations for parenteral administration may contain as common excipients sterile water or saline, alkylene glycols such as propylene glycol, polyalkylene glycols such as polyethylene glycol, oils of vegetable origin, hydrogenated naphthalenes and the like. Examples of vehicles for parenteral administration include water, aqueous vehicles such as saline, Ringer's solution, dextrose solution, and Hank's solution and nonaqueous vehicles such as fixed oils (such as corn, cottonseed, peanut, and sesame), ethyl oleate, and isopropyl myristate. Sterile saline is a preferred vehicle and the compounds are sufficiently water soluble to be made up as a solution for all foreseeable needs. The vehicle may contain minor amounts of additives such as substances that enhance solubility, isotonicity, and chemical stability, e.g., antioxidants, buffers, and preservatives. For oral administration, the formula can be enhanced by the addition of bile salts and also by the addition of acylcarnitines (*Am. J. Physiol.* 251:332 (1986)). Formulations for nasal administration may be solid and contain as excipients, for example, lactose or dextran, or may be aqueous or oily solutions for administration in the form of nasal drops or metered spray. For buccal administration typical excipients include sugars, calcium stearate, magnesium stearate, pregelatinated starch, and the like.

When formulated for nasal administration the absorption across the nasal mucous membrane is enhanced by surfactant acids, such as for example, glycocholic acid, cholic acid, taurocholic acid, ethocholic acid, desoxycholic acid, chenodesoxycholic acid, dehydrocholic acid, glycodeoxycholic acid, and the like (See, B. H. Vickery, "LHRH and its Analogs-Contraception and Therapeutic Applications", Pt. 2, B. H. Vickery and J. S. Nester, Eds., MTP Press, Lancaster, UK, 1987).

DETAILED DESCRIPTION OF THE INVENTION

The compounds of this invention were prepared by using the general synthetic methods described in the Schemes below.

In Scheme I, the desired amine (Formula 1) was either purchased commercially or prepared by reductive amination of an aldehyde (Formula 2) and an amine (Formula 3), and then acylated or sulfonylated with an appropriate acid or sulfonyl chloride. This afforded compounds of the type in Formula 4.

Alternatively (Scheme II), direct alkylation of an acylated amine (Formula 5) was performed to give differentially N,N-disubstituted amides of the type in Formula 6. The alkylation reaction proceeds nicely using potassium t-butoxide as a base and tetrahydrofuran as a solvent.

Methods for the preparation of acid chlorides, sulfonyl chlorides, reductive amination and alkylation of amines are well known in the art. See "Advanced Organic Chemistry", J. March, eds. McGraw-Hill Book Co., Second Edition, 1977.

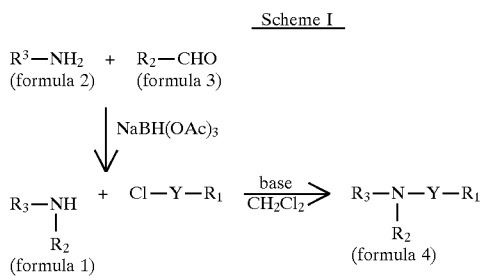

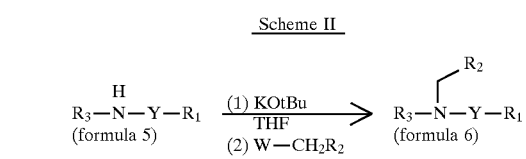

EXAMPLE 1

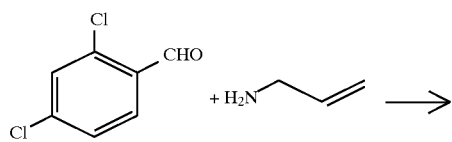

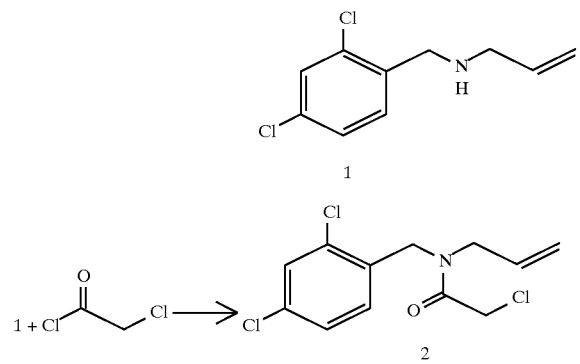

Part A: To 1 g of 2,4-dichlorobenzaldehyde in 6 mL of 1,2-dichloroethane was added 428 μL of allyl amine, 280 μL of acetic acid, and 1.8 g of NaBH(OAc)$_3$ in the given order. After 30 minutes, the reaction mixture was diluted with chloroform and saturated aqueous NaHCO$_3$. The layers were separated and the organic layer was dried (MgSO$_4$) and concentrated in vacuo affording a colorless oil. Flash chromatography (15% EtOAc-hexane) afforded 476 mg (38%) of 1 as a colorless oil.

Part B: 476 mg of 1 was dissolved in 5 mL of methylene chloride and 306 μL of Et$_3$N was added. The reaction mixture was cooled to 0° C. and 175 μL of chloroacetyl chloride was added and the mixture was stirred for 2 h. The reaction was then diluted with chloroform and washed twice with water. The combined organic layers were dried (MgSO$_4$) and concentrated in vacuo provided a white solid. Flash chromatography (15% EtOAc-hexane) afforded 500 mg of 2 as a white solid:

Low Resolution Mass Spec. m/z (relative intensity): 292 (M+H; 100), 256 (76), 174 (12), 159 (34),146 (5)

EXAMPLE 2

Preparation of N-Benzyl-N-(2,4-dichlorobenzyl) chloroacetamide (4)

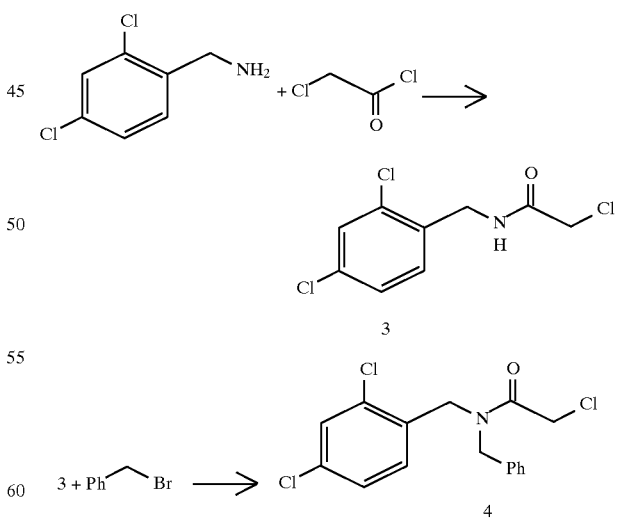

Part A: 100 g of 2,4-dichlorobenzylamine was dissolved into 600 mL of CH$_2$Cl$_2$ and the reaction mixture was cooled to 0° C. Next, 89 mL of Et$_3$N was added followed by the dropwise addition of 50 mL of chloroacetyl chloride. The reaction mixture was stirred for 24 h. The reaction was then washed twice with H$_2$O, dried (MgSO$_4$) and concentrated in vacuo affording a solid which was triturated with 10% hexane-EtOAc affording 131 g (97%) of 3 as a pure white solid.

Part B: 500 mg of 3 was dissolved in 2 mL of THF and 2 mL (10 equiv) of benzyl bromide was added. Next, 276 mg of potassium t-butoxide in 7 mL of THF was added dropwise to the reaction mixture which was then stirred for 30 minutes and finally was concentrated in vacuo. The residue was dissolved in chloroform and washed twice with H$_2$O, dried (MgSO4) and concentrated in vacuo affording a yellow oil. Flash chromatography (15% EtOAc-hexane) afforded 500 mg (73%) of 4 as a white solid.

Low Resolution Mass Spec. mlz (relative intensity):
356 (M+H; 11), 196 (4), 91 (100)

Using the methods described in Examples 1 and 2, the following were also prepared:

EXAMPLE 3
N-(2.4-Dichlorobenzyl)-N-methyl chloroacetamide
Low Resolution Mass Spec. m/z (relative intensity):
266 (M+H; 16), 232 (53), 214 (19), 188 (100), 173 (16).

EXAMPLE 4
N-Benzyl-N-(3-chlorobenzyl) chloroacetamide
Low Resolution Mass Spec. m/z (relative intensity):
308 (M+H; 36), 216 (5), 182 (17), 106 (15), 91 (100).

EXAMPLE 5
N-Benzyl-N-(2,5-dichlorobenzyl) chloroacetamide
Low Resolution Mass Spec. m/z (relative intensity):
342 (M+H; 58), 306 (15), 182 (32), 106 (23), 91 (100).

EXAMPLE 6
N-(4-Chlorobenzyl) chloroacetamide
Low Resolution Mass Spec. m/z (relative intensity):
308 (M+H; 22), 274 (13), 230 (11), 125 (90), 91 (100).

EXAMPLE 7
N-Benzyl-N-(3,4-dichlorobenzyl) chloroacetamide
Low Resolution Mass Spec. m/z (relative intensity):
342 (M+H; 20), 106 (20), 91 (100).

EXAMPLE 8
N-Benzyl-N-(2-chlorobenzyl) chloroacetamide
Low Resolution Mass Spec. m/z (relative intensity):
308 (M+H; 50), 272 (14), 182 (15), 125 (10), 106 (22), 91 (100).

EXAMPLE 9
N-Benzyl-N-(2,3-dichlorobenzyl) chloroacetamide
Low Resolution Mass Spec. m/z (relative intensity):
342 (M+H; 36), 306 (15), 182 (13), 106 (17), 91 (100).

EXAMPLE 10
N-Cyanoethyl-N-(2.4-dichlorobenzyl) methoxyacetamide
$^1$H NMR (CDCl$_3$) δ7.44–7.06 (m, 3H, Ar), 4.70 (s, 2H, (OCH$_2$—O) 4.23 and 4.11 (two singlets, 2H (rotamers), ArCH$_2$—N) 3.63 and 3.55 (two triplets, 2H (rotamers) J=6.53 Hz each, N—CH$_2$—CH$_2$) 2.68 and 2.63 (two triplets, 2H, J=6.53Hz each (rotamers) CH$_2$—CN)

EXAMPLE 11
N-Cyanomethyl-N-(2.4-dichlorobenzyl) chloromethylsulfonamide
$^1$H NMR (CDCl$_3$) δ 7.55–7.28 (m, 3H, Ar), 4.72 (s, 2H, SO$_2$CH$_2$—Cl) 4.58 (s, 2H, ArCH$_2$N) 3.70 (t, 2H, J=7.02Hz, N—CH$_2$CH$_2$) 2.61 (t, 2H, J=7.21 Hz, CH$_2$—CN).

EXAMPLE 12
N-Cyanoethyl-N-(2,4-dichlorobenzyl) propionamide
Low Resolution Mass Spec. m/z (relative intensity):
285 (M+H; 72), 249 (100),188 (7),159 (9),109 (6).

EXAMPLE 13
N-Cyanoethyl-N-(2,4-dichlorobenzyl) fluoroacetamide
Low Resolution Mass Spec. mlz (relative intensity):
289 (M+H; 100), 253 (40), 159 (20).

EXAMPLE 14
N-(2,4-Dichlorobenzyl)-N-[(3-phenyl)propyl] chloroacetamide
Low Resolution Mass Spec. m/z (relative intensity):
370 (M+H; 62), 336 (53), 302 (23), 185 (40), 159 (69), 125 (31), 93 (100).

EXAMPLE 15
[(N-Chloroacetyl)-N-(2,4-dichlorobenzyl)] glycine
Low Resolution Mass Spec. m/z (relative intensity):
311 (M+H;100), 274 (46), 232 (16),159 (11), 115 (5).

EXAMPLE 16
N-(2,4-Dichlorobenzyl)-N-[(2-thienyl)ethyl] chloroacetamide
Low Resolution Mass Spec. m/z (relative intensity):
364 (M+H; 100), 326 (7), 266 (12), 159 (29),110 (56).

EXAMPLE 17
N-(2,4-Dichlorobenzyl)-N-[(2-thienyl)methyl] chloroacetamide
$^1$H NMR (CDCl$_3$) δ 7.49–6.98 (m, 6H, Ar), 4.78 and 4.66 (two singlets, 2H (rotamers) Ar—CH$_2$—N), 4.75 (s, 2H, COCH$_2$—Cl), 4.28 and 4.12 (two singlets, 2H, N—CH$_2$—thiophene)

EXAMPLE 18
N-(3-Chlorobenzyl) chloroacetamide
Low Resolution Mass Spec. m/z (relative intensity):
218 (M+H; 80), 182 (77), 153 (11), 141 (16), 125 (100), 106 (42).

EXAMPLE 19
N-(2,3-Dichlorobenzyl) chloroacetamide
Low Resolution Mass Spec. m/z (relative intensity):
254 (M+H; 59), 216 (100), 159 (74), 106 (42).

EXAMPLE 20
N-(2,5-Dichlorobenzyl) chloroacetamide
Low Resolution Mass Spec. m/z (relative intensity):
254 (M+H; 95), 216 (100),159 (95), 141 (13), 106 (89).

EXAMPLE 21
N-(2,4-Dichlorobenzyl) chloroacetamide
Low Resolution Mass Spec. m/z (relative intensity):
252 (M+H; 38), 217 (20), 185 (43.6), 159 (25), 132 (19), 110 (20), 93 (100), 75 (32).

EXAMPLE 22
N-[(2,4-Dichlorophenyl)ethyl] chloroacetamide
Low Resolution Mass Spec. m/z (relative intensity):
266 (M+H; 23), 232 (11), 185 (56), 139 (9), 170 (13), 93 (100), 75 (24).

Compounds of the present invention were tested for IL-1β protease inhibition activity according to the following protocols:

In Vitro

Partially purified IL-1β protease is stored at −80° C., thawed on ice, and preincubated for 10 minutes at 37° C.

with 2.5 mM dithiothreitol in a buffer solution containing 10 mM Tris-HCl (pH 8.0) and 25% (v/w) glycerol. Inhibitors are prepared as stock solutions in dimethyl sulfoxide (DMSO). The protease is preincubated with inhibitor in a volume of 20 µL in a 1.5 mL polypropylene microcentrifuge tube for 15 minutes at 37° C. The volume of compound added to the assay is adjusted to yield a DMSO concentration in the preincubation of <15% (v/v). The enzyme assay is then initiated by the addition of substrate (TRITC-AYVHDAPVRS-NH$_2$) (SEQ I.D. No. 1)

Ala Tyr Val His Asp Ala Pro Val Arg Ser
1               5                       10 to yield a final concentration of 67 µM in a final volume of 30 µL. The reaction are carried out for 60 minutes at 37° C. in the dark and are terminated by the addition of 10 mL of 10% trifluoroacetic acid (TFA). Following the addition of 115 µL of 0.1 % TFA, the samples are analyzed by high pressure liquid chromatography using a reverse phase (C18) column and elution with an acetonitrile/water/TFA gradient. Substrate and product are monitored by their absorbance at 550 nm and elute at 4.2 and 5.2 minutes, respectively.

The compound in example 1 - possesses IL-1β protease inhibition ($IC_{50}$=<1.0 µM).

In Vivo

In vivo inhibition ($IC_{50}$) was determined as follows:

Human monocytes were isolated from heparinized leukopheresis units obtained through Biological Specialty Corporation (Lansdale, Pa.). Monocytes were purified by Ficoll-Hupaque (Pharmacia Fine Chemicals, Piscataway, N.J.) gradient centrifugation and more than 95% pure monocyte populations obtained by centrifugal elutriation. The assay was performed on duplicate samples of freshly isolated human monocytes, cultured in suspension at 37° C. and rotated gently in conical bottom polypropylene tubes (Sardstedt Inc., Princeton, N.J.). Human monocytes at a concentration of 5×10$^6$ cells/mL were resuspended in 1 mL of RPMI 1640 (a common tissue buffer from M.A. Bioproducts, Walkersville, Md.) containing 1% fetal calf serum (FCS) (HyClone, Logan, Utah) and 50 µg/mL gentamycin (Gibco, Grand Island, N.Y.). The cells were treated either with a compound of the invention (i.e. test compound) or with a non-inhibitor (control compound, typically 0.03% DMSO) for 15 minutes and then activated with 0.01% fixed Staphylococcus aureus (The Enzyme Center, Malden, Mass.) for 1 hour. The cells were then centrifuged and resuspended in 1 mL of cysteine, methionine-free RPMI media containing 1% dialyzed FCS (Hyclone). The cells were pretreated with a test compound or control compound for 15 minutes after which 0.01% fixed S. aureus plus 100 µCi Tran 35-S label (ICN, Irvine, Calif.) was added and the cells incubated at 37° C. for 1 hour. After incubation, cells were centrifuged, washed once in phosphate buffer saline and resuspended in 1 mL RPMI containing 1% fetal calf serum. The cells were again pretreated with a test or control compound for 15 minutes and then 0.01% S. aureus for 2 hours. At the end of the incubation, cells were centrifuged and supernates saved for immunoprecipitation. Cells were washed once in phosphate buffer saline and then lysed in RIPA, a continuous cell media buffer containing 2 mM phenylmethylsulfonyl fluoride, 10 mM iodoacetate, 1 µg/mL pepstatin A, 1 µg/mL leupeptin and 0.5 TIU aprotinin.

For the immunoprecipitations, an equal volume of 1% dry milk in RIPA buffer plus 50 µL of resuspended protein A sepharose CL-4B (Pharmacia, Piscataway, N.Y.) was added to supernates and 1 mL of 4% dry milk containing protein A sepharose CL-4B to cell lysates and samples rotated for 30 minutes at 4° C. Beads were then centrifuged down, samples transferred to fresh tubes and incubated overnight with 40 µg rabbit anti-human IL-10 polyclonal antibody (Genzyme, Cambridge, Mass.). The IL-1β proteins were then precipitated with 70 µL protein A sepharose, resuspended in 60 µL SDS sample buffer and run on 15% SGD-PAGE gels. Autoradiography was performed on dried gels and the amount of radioactivity (counts per minute, cpm) quantitated using a Betascope 603 analyzer.

Data Analysis

In the monocyte pulse chase assay, each test parameter was run in duplicate. Data was collected from the Beta Scope using a personal computer, then transferred to the VAX system for calculation of mean cpm and standard deviation of the mean. When test compounds were evaluated, the percent inhibition of release of mature IL-1β was calculated as follows:

100×[1−(cells treated with stimuli+test compound−unstimulated cells)/(cells treated with stimuli+control compound−unstimulated cells)]

These % inhibition values were then used to calculate $IC_{50}$ value for each compound. Since the human monocyte pulse chase assay uses primary cells from different donors, each test compound was run in 2–3 separate experiments, using monocytes from 2–3 different donors.

The compound in Example 1 had in vivo $IC_{50}$ of <10 µM.

---

What is claimed is:

1. A method for treating or preventing a disease selected from the group consisting of IL-1 mediated disease, infectious disease, septic shock, respiratory disease, inflammatory disease, immune-based disease, autoimmune disease, bone disease and cancer in a mammal in need of such treatment comprising the step of administering to said mammal a pharmaceutical composition comprising an effective amount of a compound of the formula (A) or a pharmaceutically acceptable salt thereof:

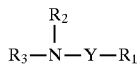 (A)

wherein:

Y is CO;

$R_1$ is alkyl, wherein the alkyl is optionally substituted with halo or alkoxy;

$R_2$ is H, alkyl, ($CH_2$)-alkenyl, aralkyl, cyanoalkyl, or aryl; and $R_3$ is aralkyl or aryl.

2. The method of claim 1 comprising said compound of formula (A) or a pharmaceutically acceptable salt thereof: wherein:

$R_1$ is alkyl, substituted with halo;

$R_2$ is ($CH_2$)-alkenyl or aralkyl; and $R_3$=aralkyl.

3. The method according to claim 1, wherein the compound is N-Allyl-N-(2,4-dichlorobenzyl) chloroacetamide, N-Benzyl-N-(2,4-dichlorobenzyl) chloroacetamide, N-Benzyl-N-(3-chlorobenzyl)chloroacetamide, N-Benzyl-N-(2,5-dichlorobenzyl)chloroacetamide, N-Benzyl-N-(3,4-dichlorobenzyl)chloroacetamide, N-Benzyl-N-(2-chlorobenzyl)chloroacetamide, N-Benzyl-N-(2,3-dichlorobenzyl chloroacetamide.

4. The method according to claim 1, wherein the compound is N-Cyanoethyl-N-(2,4-dichlorobenzyl) methoxyacetamide, N-Cyanomethyl-N-(2,4-dichlorobenzyl) chloromethylsulfonamide, N-Cyanoethyl-N-(2,4-dichlorobenzyl) propionamide, or. N-Cyanoethyl-N-(2,4-dichlorobenzyl) fluoroacetamide.

5. The method according to claim 1, wherein the compound is N-(2,4-Dichlorobenzyl)-N-methyl chloroacetamide, N-(4-Chlorobenzyl)chloroacetamide, N-(3-chlorobenzyl)chloroacetamide, N-(2,3-dichlorobenzyl)chloroacetamide, N-(2,5-dichlorobenzyl) chloroacetamide, or N-(2,4-dichlorobenzyl) chloroacetamide.

6. The method according to claim 1, wherein the compound is N-(2,4-Dichlorobenzyl)-N-[(3-phenyl) propyl] chloroacetamide, [(N-Chloroacetyl)-N-(2,4-dichlorobenzyl)]glycine, N-(2,4-dichlorobenzyl)-N-[(2-thienyl)ethyl] chloroacetamide, N-(2,4-dichlorobenzyl)-N-[(2-thienyl) methyl]chloroacetamide, or N-[(2,4-dichlorophenyl)-ethyl] chloroacetamide.

7. The method according to claim 1, wherein the inflammatory disease is a lung, central nervous system, or connective tissue disease.

8. The method according to claim 1, wherein the immune-based disease is a lung, central nervous system, or connective tissue disease.

9. The method according to claim 1, wherein the infectious disease is meningitis or salpingitis.

10. The method according to claim 1, wherein the inflammatory disease is arthritis, cholangitis, colitis, encephalitis, endocerolitis, hepatitis, pancreatitis, or reperfusion injury.

11. The method according to claim 1, wherein the immune-based disease is hypersensitivity.

12. The method according to claim 1, wherein the autoimmune disease is multiple sclerosis.

* * * * *